United States Patent [19]

Indig et al.

[11] Patent Number: 4,978,921
[45] Date of Patent: Dec. 18, 1990

[54] ELECTRODE PROBE FOR USE IN AQUEOUS ENVIRONMENTS OF HIGH TEMPERATURE AND HIGH RADIATION

[75] Inventors: Maurice E. Indig, Fremont, Calif.; Laura L. H. King, Raleigh, N.C.

[73] Assignee: General Electric Company, San Jose, Calif.

[21] Appl. No.: 345,738

[22] Filed: May 1, 1989

[51] Int. Cl.$^5$ ............................................. G01N 27/02
[52] U.S. Cl. ................................... 324/446; 204/400; 324/724; 324/72.5
[58] Field of Search ............. 324/446, 438, 439, 72.5, 324/700, 713, 724, 158 P, 149; 204/1 T, 406, 400

[56] References Cited

U.S. PATENT DOCUMENTS

| | | | |
|---|---|---|---|
| 2,229,036 | 1/1941 | Bird et al. | 324/446 X |
| 3,772,591 | 11/1973 | Louder et al. | 324/446 |
| 3,794,913 | 2/1974 | Cropper et al. | 324/724 X |
| 4,003,814 | 1/1977 | Tarassoff et al. | 324/446 X |
| 4,329,644 | 5/1982 | Libertini et al. | 324/166 X |
| 4,467,658 | 8/1984 | Dube et al. | 324/446 X |
| 4,550,273 | 10/1985 | Boettcher et al. | 324/403 X |
| 4,788,506 | 11/1988 | Weissmann | 324/446 |
| 4,839,580 | 6/1989 | Moore et al. | 324/700 X |

Primary Examiner—Reinhard J. Eisenzopf
Assistant Examiner—Robert W. Mueller
Attorney, Agent, or Firm—Robert R. Schroeder

[57] ABSTRACT

Disclosed is an electrode probe for employment in monitoring electrochemical potentials and which has a robust structure particularly suiting it for employment within the rigorous environment of the reactor core of a nuclear power facility. The electrode of the present invention is comprised of four major segments: a metal cap electrode, an alumina retainer, an annular metal sleeve, and a positioning and signal transfer assembly. The metal cap electrode has a tip portion and an annulus extending therefrom which defines a cavity having an interior surface. The alumina retainer has a base region with a sleeve attachment surface, an oppositely disposed cap securing portion nestably disposed within said cap electrode cavity and sealingly attached thereto. The retainer further has an axis channel penetrating therethrough from the base region to the cap securing portion. The annular metal sleeve is formed of metal exhibiting a coefficient of thermal expansion compatible with the alumina retainer and has an alumina retainer surface in sealing engagement with said retainer sleeve attachment surface and oppositely disposed outlet. An electrical conductor is in electrical connection with the cap electrode and extends through the retainer access channel and through the annular metal sleeve to the sleeve outlet. Finally, positioning and signal transfer assembly is associated with the sleeve outlet for providing support for the sleeve and for conveying electrical signals from the conductor.

17 Claims, 2 Drawing Sheets

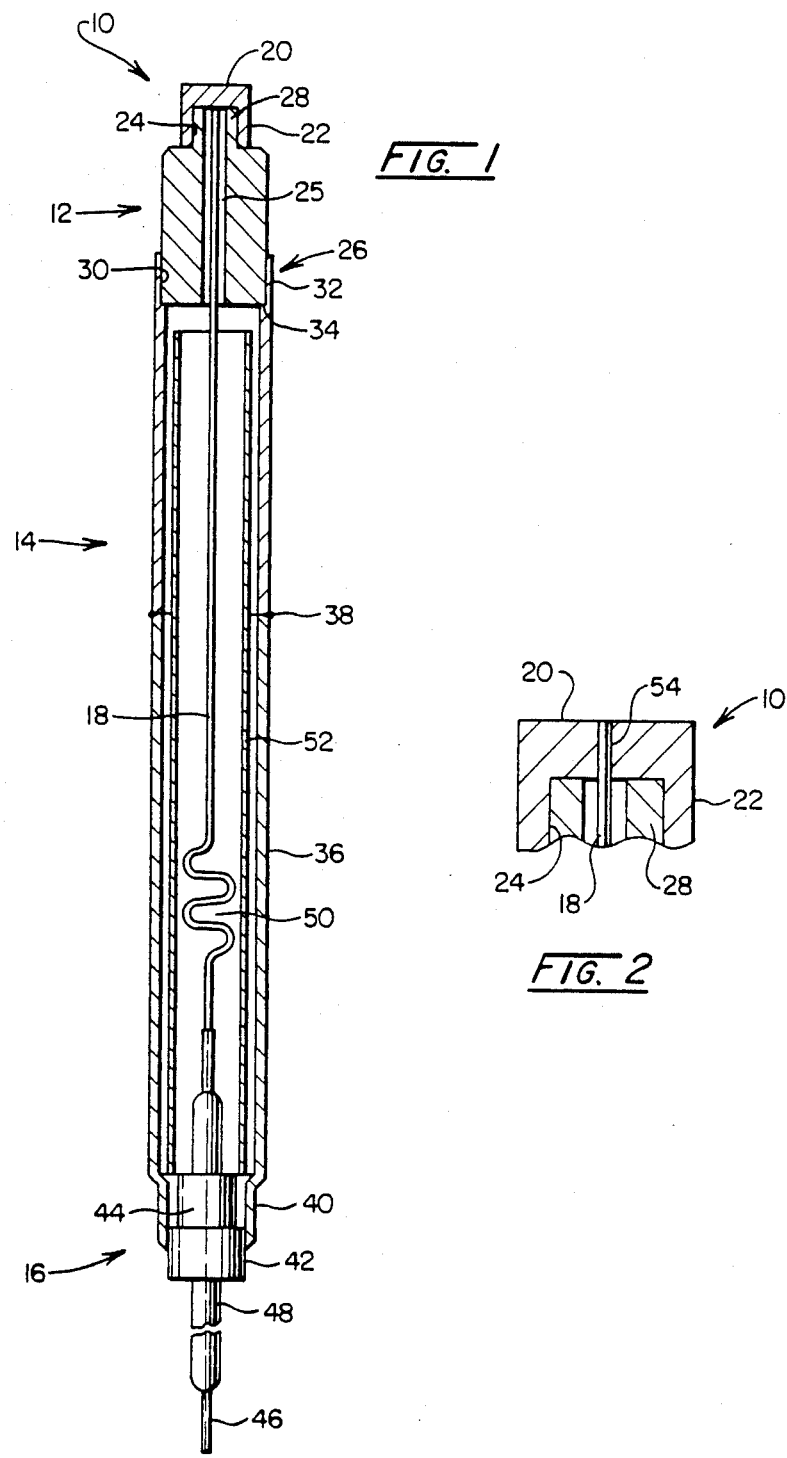

ELECTRODE PROBE FOR USE IN AQUEOUS ENVIRONMENTS OF HIGH TEMPERATURE AND HIGH RADIATION

BACKGROUND OF THE INVENTION

The nuclear power industry long has been engaged in a multitude of studies and investigations seeking improvement in the stamina and reliability of the materials and components forming a reactor based power system. One such investigation has been concerned with intergranular stress corrosion cracking (IGSCC) which heretofore principally has been manifested in the water recirculation piping systems external to the radiation intense reactor core regions of nuclear facilities. Typically, the piping architecture of these external systems is formed of a stainless steel material. Generally, these studies have determined that three factors must occur in coincidence to create IGSCC promotional conditions. These factors are: (a) a sensitization of the metal (stainless steel) for example, such as caused by a chromium depletion at grain boundaries which may be caused by heat treatment in the course of normal processing of the material or by welding and the like procedures; (b) the presence of tensile stress in the material; and (c) the oxygenated normal water chemistry (NWC) environment typically present in a boiling water reactor (BWR). This latter environment is occasioned by any of a variety of oxidizing species contributed by impurities in reactor coolant water. By removing any one of these three factors, the IGSCC phenomenon is essentially obviated. Such removal particularly has been accomplished with respect to the latter, oxygenated environment factor, through employment of an electrochemical potential monitoring approach combined with an associated hydrogen water chemistry (HWC) technique providing for a controlled addition or injection of hydrogen into the aqueous coolant environment.

Electrochemical potential monitoring is carried out employing paired electrochemical half-cell probes or electrodes which are mounted within the recirculation piping or in an external vessel which has its water source from the reactor water in the recirculation piping the electrodes are accessed to the external environment through gland type mountings or the like. Where, as in the instant application, the electrode system of interest involves the potential from a metal corrosion electrode, then the reference electrode can conveniently be a metal-insoluble salt-electrode if the metal salt couple is chemically stable and if appropriate thermodynamic data is available. Accordingly, one of the thus-mounted probes which is configured as a reference electrode may be based, for example, on a silver/silver chloride half-cell reaction. Once the reference electrode half cell is defined, the cell is completed with the sensing cell portion based upon a metal such as platinum or stainless steel. Calibration of the reference electrode and/or the electrode pair is carried out by appropriate Nernst based electrochemical calculations, and by thermodynamic evaluation in combination with laboratory testing within a known environment.

Half cell electrodes developed for use in reactor recirculation piping traditionally have been configured with metal housings, high temperature ceramics, and polymeric seals such as Teflon. These structures have performed adequately in the more benign and essentially radiation-free environments of recirculation piping.

Over the recent past, investigators have sought to expand the electrochemical potential (ECP) monitoring procedures to the severe environment of the fluid in the vicinity of the reactor core itself for the purpose of studying or quantifying the effect of hydrogen-water chemistry adjustment in mitigating irradiation assisted stress corrosion cracking (IASCC) as well as IGSCC. Within the reactor core, the monitoring electrode can be mounted, for example, with otherwise unemployed or in tandem with the traveling instrumentation probe (TIP) of available local power range monitors (LPRM) and the like. The monitors are located in a severe, high temperature (typically 285° C.), high pressure and high radiation (typically $10^9 R$ (rads) per hour gamma, $10^{13} R$ per hour neutron) environments. Probe structures of earlier designs are completely inadequate for this reactor core environment, both from a material standpoint and with respect to the critical need to prevent leakage of radioactive materials to the environment outside of the reactor vessel.

BROAD STATEMENT OF THE INVENTION

The present invention is addressed to an electrode for evaluating electrochemical potentials which has a robust structure particularly suiting it for employment within the rigorous environment of the reactor core of a nuclear power facility.

The electrode of the present invention is comprised of four major segments: a metal cap electrode, an alumina retainer (i.e. an insulator), an annular metal sleeve, and a positioning and signal transfer assembly. The metal cap electrode has a tip portion and an annulus extending therefrom which defines a cavity having an interior surface. The alumina retainer has a base region with a sleeve attachment surface, an oppositely disposed cap securing portion nestably disposed within said cap electrode cavity and sealingly attached thereto. The retainer further has an axis channel penetrating therethrough from the base region to the cap securing portion. The annular metal sleeve is formed of metal exhibiting a coefficient of thermal expansion compatible with the alumina retainer and has an alumina retainer surface in sealing engagement with said retainer sleeve attachment surface and oppositely disposed outlet. An electrical conductor is in electrical connection with the cap electrode and extends through the retainer access channel and through the annular metal sleeve to the sleeve outlet. Finally, positioning and signal transfer assembly is associated with the sleeve outlet for providing support for the sleeve and for conveying electrical signals from the conductor.

Advantages of the present invention include a probe structure adapted to operate under the rigorous environment of the reactor core of a nuclear power facility. Another advantage is the ceramic/metal construction of the electrode for providing a sealing architecture that has multiple seals to prevent leakage of radioactive materials to the ambient environment of the reactor. These and other advantages will be readily apparent to those skilled in the art based upon the disclosure contained herein.

BRIEF DESCRIPTION OF THE DRAWINGS

FIG. 1 is a cross-sectional elevation view of an electrode probe according to the invention;

FIG. 2 is an alternative metal cap electrode for use with the probe depicted at FIG. 1.

DETAILED DESCRIPTION OF THE INVENTION

Figure 3:
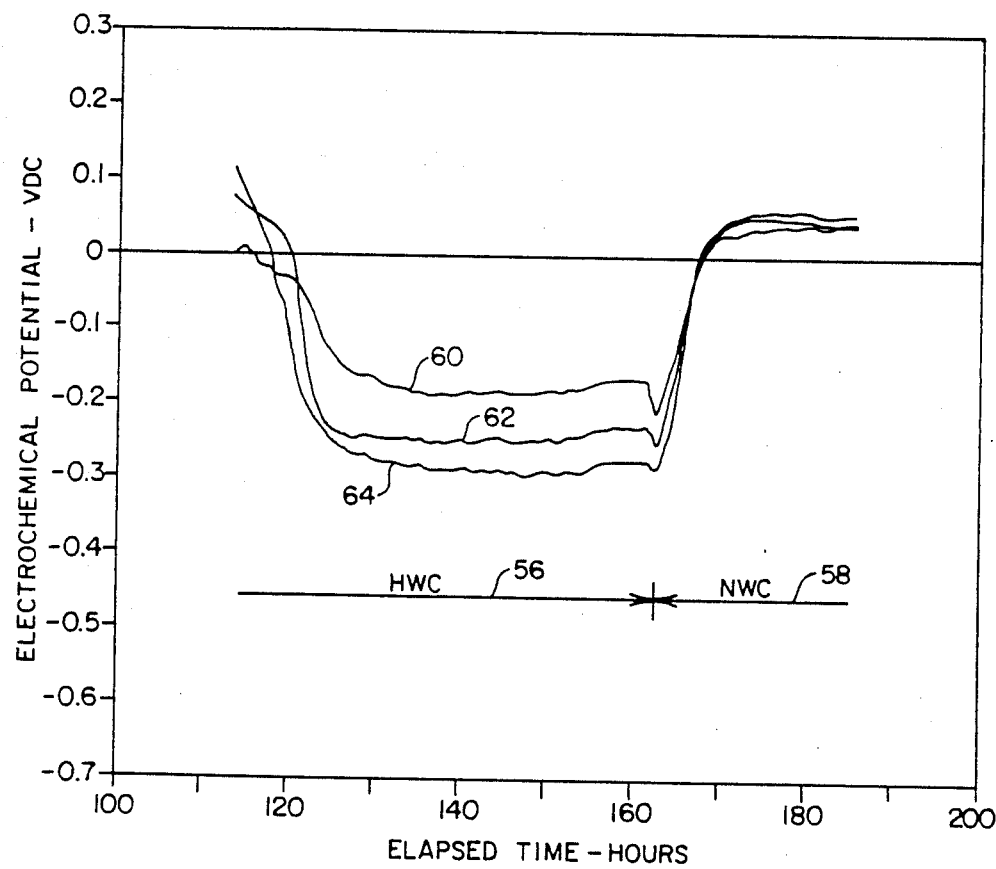
FIG. 3. is a graph showing a laboratory evaluation of an electrode according to the invention in conjunction with a standard electrode.

While having utility in a broad variety of industrial monitoring functions, the electrode structure of the instant invention finds particular utility operating under the rigorous environment of the reactor core of a nuclear power facility. No elastomeric seals or polymeric components are present in its structure which incorporates a sealing architecture of the highest integrity. In the latter regard, a brazed and welded assembly consisting only of ceramic and metal parts forms the structure of the device. The electrode finds employment either as a standard or reference electrode, or as a sensing electrode depending upon the material used in forming the active electrode area. For a detailed discussion in connection with the above, reference is made to *Physical Chemistry* by G. W. Castellan, Chapter 17, "Equilibria in Electrochemical Cells", pp 344–382, Addison-Wesley Publishing Co., Reading, Mass. (1964).

Referring to FIG. 1, the structure of the electrode probe of the present invention is seen to be comprised of four principal components: metal cap electrode 10; alumina retainer 12; annular metal sleeve 14; and positioning and signal transfer assembly 16. Electrical signals are transferred from metal cap electrode 10 through positioning and signal transfer assembly 16 to the outside via electrical conductor 18.

Referring to the various components in more detail, metal cap electrode 10 can be seen to be formed of tip portion 20 and annulus 22 that extends therefrom and which defines a cavity having an interior surface 24. Materials of construction for metal cap electrode 10 will determine the function of the electrode device of the present invention. For typicallyencountered boiling water reactor (BWR) applications, use of stainless steel in constructing metal cap electrode 10 enables the electrode probe to measure the ECP of stainless steel in any given environment. Metal cap electrodes fabricated from other materials could be used to form similar sensing electrodes for measurement of ECPs of different metals. The second general category for the electrode device of the present invention involves the use of platinum in fabricating metal cap electrode 10. Such an electrode device in HWC environments enables the use of the electrode device as a reference electrode (provided the hydrogen concentration is known) or it can be used to calibrate other reference electrodes (e.g. an Ag/AgCl reference electrode). Thus it will be seen that the architecture of the electrode probe of the present invention provides design flexibility enabling it to be adapted to function both as a sensing electrode as well as a reference electrode, while retaining the same overall construction advantages.

In order to provide electrical isolation of metal cap electrode 10 from other metal components forming the electrode probe, alumina retainer 12 is used to support metal cap electrode 10. Alumina retainer 12 desirably is formed of sapphire, which is a single crystal form of alumina. Sapphire material not only provides requisite electrical insulation, but also, by virtue of its single crystal structure, is highly resistant to attack by water within which it is immersed and, importantly, it exhibits no grain boundaries. High purity alumina, ruby, or other materials, of course, can be used as those skilled in the art will appreciate. Alumina retainer 12 is seen to be formed having base region 26 and oppositely-disposed cap securing portion 28. Cap securing portion 28 is nestably disposed within metal cap electrode 10 and in sealing engagement with cavity interior surface 24. Advantageously, interior surface 24 of annulus 22 is brazed to retainer cap securing portion 28, e.g. by use of silver braze. In this regard, it will be appreciated that all ceramic surfaces to be brazed are metalized, e.g. with tungsten and plated with nickel, in order to ensure adequate wetting of the surfaces to be attached by the braze filler metal or alloy. In fact, use of multiple layers of metal coating, especially on the mating surfaces of metal cap 28 and alumina retainer 12, can be practiced as is necessary, desirable, or convenient in conventional fashion. The braze seal between metal cap electrode 10 and alumina retainer 12 should provide a hermetic seal for ensuring integrity of the electrode probe structure and to ensure against leakage of radiation to the outside environment. To this end, the attachment regions of retainer 12 desirably are painted with tungsten paint, fired, and then nickel plated.

Base region 26 of alumina retainer 12 has sleeve attachment region 30 for securing retainer 12 to annular metal sleeve 14. Again, surface metalization and brazing with silver braze or the like is practiced for joining attachment region 30 to sleeve 14. Retainer 12 also has access channel 25 which runs its extent from cap securing portion 28 to base region 26. Again, it will be appreciated that a hermetic seal needs to be formed. Sleeve attachment region 30, then, preferably is nickel-plated, fired, and this sequence repeated.

Annular metal sleeve 14 has alumina retainer region 32 for joining with retainer sleeve attachment region 30. In the construction architecture depicted at FIG. 1, sleeve retainer region 32 is formed to have land 34 against which retainer 12 rests. It should be observed that the dimensional tolerances for all components to be joined is such that snug interengagement results, thus minimizing the volume to be filled by the braze metal used in joining the various components forming the electrode device of the present invention.

In order to minimize thermal stress which otherwise would be caused by virtue of the different materials of construction used in forming retainer 12 and annular sleeve 14, annular metal sleeve 14 is formed of a metal exhibiting a coefficient of thermal expansion compatible with the alumina retainer. Kovar comprises the preferred metal for use in forming annular metal sleeve 14. Kovar comprises a group of alloys, e.g. Fe 53.8%, Ni 29%, Co 17%, and Mn 0.2%, which exhibit a coefficient of thermal expansion compatible with that of the alumina materials used in forming retainer 12. Other materials may be used in forming annular metal sleeve 14, providing that the coefficient of thermal expansion between the materials is carefully matched. It may be observed that annular sleeve 14 could be formed of ceramic material, though cost considerations, material handling and forming operations, and the like necessitate the use of metal for the bulk of the structure of the electrode device. Thus, the use of kovar in forming annular sleeve 14.

Annular sleeve 14 may be of an extent such that its outlet bears positioning and signal transfer assembly 16. While this construction is possible, it also is possible to reduce material costs by joining kovar annular sleeve 14 with annular transition sleeve 36 that can be formed of stainless steel or other high performance alloy. Kovar sleeve 14 can be joined to stainless steel sleeve 36 at juncture 38 by use of tungsten inert gas (TIG) welding techniques. Again, a hermetic seal needs to result when joining sleeve 14 to sleeve 36.

It will be observed that the components thus-far described preferably are cylindrical in shape, though it will be appreciated that sleeves 14 and 36, and retainer 12 can be square, hexagonal, or of other geometric configuration. For that matter, the same geometric variation also applies to cap electrode 20.

The lower end of stainless steel annular sleeve 36 is seen to terminate with neck 40 which serves as the outlet for sleeve 36. Positioning and signal transfer assembly 16 is associated with neck 40 of annular sleeve 36 and is seen to be formed from cylindrical stainless steel collar 42, such as by TIG welding. Ceramic support 44, inwardly adjacent to collar 42, houses electrical connection from the outside to the interior of the electrode probe of the present invention. Specifically, insulated retainer 48 houses a nickel tube which is connected at its lower end to the current conducting wire of cable 46 and to its upper end to electrical conductor 18. Assembly 16 is commercially available and marketed, for example, by ReutorStokes, a division of General Electric Company, Twinsburg, Ohio.

In order for electrical connection to be maintained between electrode cap 10 and cable 46, electrical conductor 18 is provided, preferably with spring section or coil 50 to ensure that the electrical conductor is pushing against cap 20 and assembly 16, thus ensuring good electrical connection. Conductor 18 suitably can be made from copper, kovar, platinum, or other material which is electrically conductive. While an electrical conductor can be insulated directly, the preferred structure depicted at FIG. 1 shows annular electrical insulator 52 disposed within annular sleeve 14 and annular sleeve 36. Electrical insulator 52 preferably is made from a ceramic material, such as alumina, in order to ensure electrical isolation of electrical conductor 18. While the proximal end of electrical conductor 18 is electrically connected to assembly 16, the distal end of electrical conductor 18 passes through the annulus formed within sleeves 36 and 14, thence through access channel 25 provided in retainer 12 to cap electrode 20. Conductor 18 preferably is welded or brazed directly to the interior side of tip portion 20 of cap electrode 10. Alternatively, as depicted at FIG. 2, cap electrode 10 can have hole 54 penetrating through tip portion 20. Conductor 18 would be placed within hole 54 and brazed or welded in place to provide electrical connection therewith. The integrity of the seal, again, should be hermetic in nature.

With respect to performance specifications of the inventive electrode probe, the probe is designed to operate at temperatures ranging up to about 600° F. and pressures of up to about 2,000 psi. When metal cap electrode 10 is formed of platinum for producing the reference electrode device, the novel electrode device exhibits a voltage that is within ±0.020 volts of the theoretical value for the platinum reference electrode. In use as a reference electrode with a platinum cap, the inventive electrode probe is capable of measuring ECPs to within ±0.010 volts in constant water chemistry. In attaching cap 10 manufactured of platinum, it should be rhodium plated and then silver brazed to W/Ni coated cap securing portion 28.

Referring to FIG. 3, two sensing electrode probes were fabricated in accordance with the precepts of the invention utilizing stainless steel for metal cap electrode 10 and these probes subjected to laboratory testing utilizing a standard $Cu/Cu_2O$ reference electrode. The aqueous medium for testing was provided by an autoclave within which temperature and water chemistry were controlled. The test was carried out at a water temperature of 274° C. and in conjunction with a sequence of aqueous conditions wherein certain dissolved gases were introduced. A first such dissolved gas was hydrogen, as labeled along the elapsed time portion of the figure as represented at 56, and represents hydrogen water chemistry. Thereafter, as labeled along the elapsed time portion of the figure as represented at 58, oxygen was injected into the aqueous medium, thus subjecting the probes to normal boiling water chemistry. As the potential of the reference electrode can be calculated, its potential under the various water conditions can be subtracted from the voltage obtained, thus enabling a measurement of the ECP of the stainless steel electrode probes. The results of the three probes evaluated are represented at 60, 62, and 64. It will be observed that a shift in the ECP results by virtue of the water chemistry involved. It is this shift that is monitored during use of the sensing electrode probes for determining the water chemistry of the aqueous medium being tested. The expected shift in ECP can be seen by reference to FIG. 3.

Since certain changes may be made in the above-described apparatus without departing from the scope of the invention, the description and accompanying drawings shall be interpreted as illustrative and not in a limiting sense in accordance with the precepts of the invention disclosed herein.

We claim:

1. An electrode probe for employment in monitoring electrochemical potentials, comprising:
   (a) a metal cap electrode having a tip portion, and an annulus extending therefrom which defines a cavity having an interior surface;
   (b) an alumina retainer having a base with a sleeve attachment region and oppositely disposed cap securing portion nestably disposed within said cap electrode cavity and sealingly attached thereto, and an access channel penetrating therethrough from said base to said cap securing portion;
   (c) a first annular metal sleeve formed of a metal exhibiting a coefficient of expansion compatible with said alumina retainer, and having an alumina retainer region in sealing engagement with said retainer sleeve attachment region, said sleeve having an oppositely disposed outlet;
   (d) a first insulated electrical conductor in electrical connection with said cap electrode and extending through said retainer access channel and through said annular metal sleeve to said sleeve outlet; and
   (e) a positioning and signal transfer assembly associated with said sleeve outlet for providing support for said sleeve and for conveying electrical signals from said conductor.

2. The electrode probe of claim 2 wherein said first electrical conductor is insulated by an annular electrical insulator housed within said first annular metal sleeve.

3. The electrode probe of claim 2 wherein said annular electrical insulator is formed of alumina.

4. The electrode probe of claim 1 wherein said positioning and signal transfer assembly includes an annular stainless steel collar welded to the outlet of said first annular metal sleeve and through which an insulated second electrical conductor passes, said second electrical conductor being electrically connected to said first electrical conductor.

5. The electrode probe of claim 1 wherein a second annular metal transition sleeve is interposed between said first annular metal sleeve and said positioning and signal transfer assembly, said second metal transition sleeve being formed of a different material than said first annular metal sleeve.

6. The electrode probe of claim 5 wherein said second metal transition sleeve is formed of stainless steel.

7. The electrode probe of claim 1 wherein said first electrical conductor is a wire formed of a material selected from the group consisting of platinum, a kovar, and copper.

8. The electrode probe of claim 1 wherein said metal cap electrode is formed of a material selected from the group consisting of stainless steel and platinum.

9. The electrode probe of claim 1 wherein said first annular metal sleeve is formed of kovar.

10. The electrode probe of claim 1 wherein said alumina retainer is formed from single crystal sapphire.

11. An electrode probe for employment in monitoring electrochemical potentials, comprising:
(a) a cylindrical metal cap electrode having a tip portion, and an annulus extending therefrom which defines a cavity having an interior surface;
(b) a cylindrically-shaped alumina retainer having a base with a sleeve attachment region and oppositely disposed cap securing portion nestably disposed within said cap electrode cavity and sealingly brazed thereto, and an access channel penetrating therethrough from said base to said cap securing portion;
(c) a kovar annular cylindrical sleeve having an alumina retainer region in sealing brazed engagement with said retainer sleeve attachment region, said sleeve having an oppositely disposed outlet;
(d) an annular ceramic electrical insulating cylinder housed within said kovar annular cylinder substantially its entire extent;
(e) a first electrical conductor wire in electrical connection with said cap electrode and extending through said retainer access channel and through said ceramic cylinder to said sleeve outlet; and
(f) a metal collar welded to the outlet of said sleeve and through which a second insulated conductor wire passes from without to within said annular ceramic cylinder to electrical connection with said first electrical conductor wire.

12. The electrode probe of claim 11 wherein a stainless steel annular transition sleeve is welded to said kovar annular cylinder, said transition sleeve having an outlet to which said metal collar is welded.

13. The electrode probe of claim 12 wherein said alumina retainer is formed of a single crystal sapphire.

14. The electrode probe of claim 13 wherein said first conductor wire is formed of a material selected from the group consisting of platinum, kovar, and copper.

15. The electrode probe of claim 14 wherein said metal cap electrode is formed from a material selected from the group consisting of stainless steel and platinum.

16. The electrode probe of claim 11 wherein all surfaces to be joined are metalized prior thereto.

17. The electrode probe of claim 11 wherein said first conductor wire has a spring section formed at a location within said annular ceramic cylinder.

* * * * *